Figure 1:
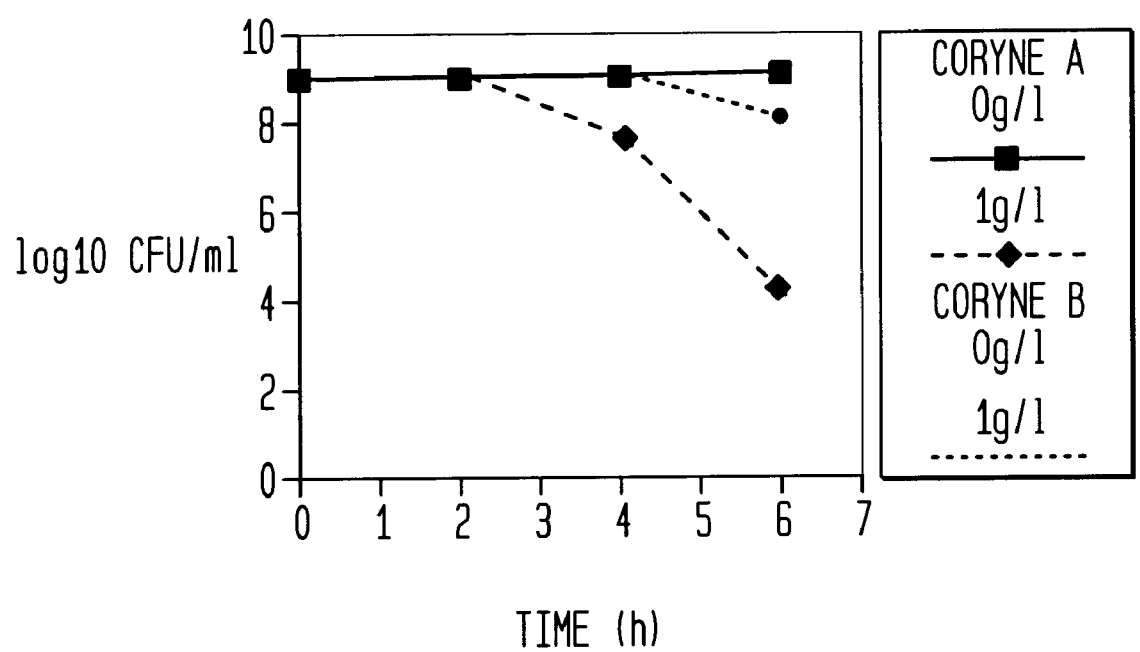

United States Patent

Casey et al.

[11] Patent Number: 6,162,422
[45] Date of Patent: Dec. 19, 2000

[54] METHOD OF REDUCING OR PREVENTING MALODOUR

[75] Inventors: John Casey, Bebington; Jayne Elizabeth Ellis, Bedford; Della Hyliands, Bedford; Alexander Gordon James, Bedford; Gary Mycock, Bedford; David Taylor, Wirral, all of United Kingdom

[73] Assignee: Unilever Home & Personal Care USA, division of Conopco, Inc., Chicago, Ill.

[21] Appl. No.: 09/348,607

[22] Filed: Jul. 6, 1999

[30] Foreign Application Priority Data

Jul. 7, 1998 [GB] United Kingdom .................. 9814731

[51] Int. Cl.⁷ ................................ A61K 7/32; A61K 7/00
[52] U.S. Cl. .......................... 424/65; 424/400; 424/401
[58] Field of Search .............................. 424/65, 400, 401

[56] References Cited

U.S. PATENT DOCUMENTS

| | | | |
|---|---|---|---|
| 4,005,189 | 1/1977 | Reese et al. | 424/65 |
| 4,356,190 | 10/1982 | Kraskin et al. | 424/319 |
| 5,587,152 | 12/1996 | Mackles et al. | 424/65 |

FOREIGN PATENT DOCUMENTS

| | | |
|---|---|---|
| 0750903 | 1/1976 | European Pat. Off. . |
| 19620644 | 11/1997 | Germany . |
| 002117946 | 5/1996 | Japan . |
| 97/44006 | 11/1997 | WIPO . |
| 98/58010 | 12/1998 | WIPO . |

OTHER PUBLICATIONS

International Search Report Application No. PCT/GB 99/02172 mailed Nov. 16, 1999.
U.S. application No. 09/348,606, Casey et al., filed Jul. 6, 1999, Cosmetic Composition.
U.S. application No. 09/348,608, Casey et al., filed Jul. 6, 1999, Method of Reducing or Preventing Malodour.
U.S. application No. 09/348,609, Casey et al., filed Jul. 6, 1999, Method of Reducing or Preventing Malodour.

*Primary Examiner*—Shelley A. Dodson
*Attorney, Agent, or Firm*—Matthew Boxer

[57] ABSTRACT

Cosmetic method for reducing or preventing malodour by topically applying to human skin an active agent capable of inactivating body malodour-causing microorganisms comprising corynebacteria, characterised in that the agent is capable of inactivating, of the corynebacteria, only those corynebacteria capable of catabolising fatty acids.

5 Claims, 1 Drawing Sheet

METHOD OF REDUCING OR PREVENTING MALODOUR

The invention relates to a cosmetic method for reducing or preventing body malodour.

In particular, it relates to a cosmetic method for reducing or preventing body malodour by topically applying to human skin an active agent capable of inactivating body malodour causing micro-organisms comprising corynebacteria, characterised in that the agent is capable of selectively inactivating, of the corynebacteria, only those corynebacteria capable of catabolising fatty acids.

It is well known that freshly secreted sweat is sterile and that body malodour is the result of biotransformation of the sweat by micro-organisms living on the surface of the skin to produce volatile odoriferous compounds.

There are three types of composition routinely used to combat body malodour: perfumes, antiperspirants and deodorants.

Perfumes are designed simply to mask body malodour.

Antiperspirant actives work by blocking the sweat glands thereby reducing perspiration. However, even the best cosmetically acceptable antiperspirant actives rarely reduce sweat production by more than 50%.

Deodorant actives, on the other hand, are designed to reduce the population of micro-organisms living on the surface of the skin. Typical deodorants include ethanol and triclosan (2,4,4'-trichloro, 2'-hydroxy-diphenyl ether) which is a well known antimicrobial agent. The skin is host to a number of microorganisms some of which are beneficial and others which are not. The use of common deodorant actives results in the indiscriminate killing of most of the skin's natural microflora including the beneficial species. This is considered an undesirable side effect of such deodorant formulations.

Some disclosures describe the use of antimicrobial substances which are selective against odour-producing bacteria.

WO 90/15077 (Gillette) describes the use of antibodies to a carrier or transport protein of coryneform bacteria and staphylococci. It is disclosed that these bacterial types have an amino acid lyase enzyme which is responsible for the formation of malodour.

Coryneform bacteria are a group of bacteria including Actinomyces, Arachnia, Arcanobacterium, Arthobacter, Bacterionema, Bifidobacterium, Brevibacterium, Cellulomonas, Corynebacterium, Eyrsipelothrix, Eubacterium, Kurthia, Listeria, Mycobacterium, Nocardia, Cerskovia, Propionibacterium, Rhodococcus and Rothia. (The Skin Microflora and Microbial Skin Disease, W C Noble. Cambridge University Press 1992). Coryneform bacteria are believed to contribute to the formation of body malodour.

DE 43 39 605 (Beiersdorf) describes the use of deodorising mixtures of alpha-omega alkane dioic acids and fatty acid partial glycerides of unbranched fatty acids which may be present in a suitable cosmetic vehicle to combat Gram positive, particularly coryneform, bacteria.

Woolwax acids have been disclosed in the following Beiersdorf publications as deodorant actives in combination with:
  alpha-omega alkane dioic acids (DE 43 24 219);
  partial glycerides of unbranched fatty acids (DE 43 09 372); or
  monocarboxylic acids, especially unbranched fatty acids (DE 43 05 889).

Each combination is described as suitable to combat Gram-positive, especially coryneform bacteria.

DE 42 37 081 (Beiersdorf) describes deodorant compositions comprising monocarboxylic acid diglycerides and/or triglycerides. The compositions are said to be suitable against Gram-positive, especially coryneform, bacteria.

EP-A-0 697 213 (Beiersdorf) describes the selective reduction of coryneform bacteria using a mixture of:
  lauric acid,
  one other fatty acid C6–C20 (one of which must be at least C12);
  glyceryl monocaprate/glyceryl monocaprylate;
  without the use of ethoxylated glyceryl fatty acid esters and propoxylated glyceryl fatty acid esters;
which has a pH of less than 8.

WO 94/07837 (Unichema) describes certain novel unsaturated dioic acids having between 8 and 12 carbon atoms. Also described is their potential use to treat malodour.

EP-A-0 750 903 (Coöperatie Cosun UA) discloses deodorant compositions comprising sugar-fatty acid esters. The actives are described as being selective towards odour-causing microorganisms. These odour-causing microorganisms are said to be the Corynebacterium varieties known as lipophilic diphtheroids such as *Corynebacterium xerosis* and *C. minutissimum*.

We have now found that the Corynebacterium genus can be subdivided into 2 subgroups according to ability to catabolise fatty acids and that one of these subgroups, hereinafter referred to as "corynebacteria A", which is capable of catabolising fatty acids, contributes strongly to the formation of body malodour, in particular axillary malodour, while the other subgroup, hereinafter referred to as "corynebacteria B", which catabolises fatty acids much less so or not at all, contributes much less or even not substantially to malodour formation. We also found that it is possible to selectively inactivate corynebacteria A as compared to corynebacteria B.

We further found that on average there is a difference between the axillary microflora of males and females and in the typical strength and nature of male and female malodour, in particular axillary malodour. Whereas for females corynebacteria A tend to comprise a smaller proportion of the axially microflora, we found that for many males malodour formation is largely caused by corynebacteria A.

By corynebacteria is meant all strains of the Corynebacterium genus.

The deodorants available on the market tend to be insufficiently effective or substantially reduce the numbers of all bacteria in the microflora indiscriminately. The present invention offers the opportunity to provide deodorant products which for many females will substantially reduce malodour formation while inactivating only a minor portion of the microflora. For many males malodour formation can be substantially reduced or even largely eliminated while inactivating only one subgroup of the microflora, the corynebacteria A.

Furthermore, we found a range of preferred specific active ingredients for selectively inactivating corynebacteria A, while leaving other bacteria, notably corynebacteria A much less affected or even not notably affected at all.

Accordingly, the invention provides a cosmetic method for reducing or preventing body malodour by topically applying to human skin an active agent capable of inactivating body malodour causing micro-organisms comprising corynebacteria, characterised in that the agent is capable of selectively inactivating, of the corynebacteria, only those corynebacteria capable of catabolising fatty acids.

The invention also provides the use of an active agent capable of inactivating body malodour causing microorganisms comprising corynebacteria in the manufacture of a cosmetic composition for reducing or preventing body malodour, characterised in that the agent is capable of selectively inactivating, of the corynebacteria, only those corynebacteria capable of catabolising fatty acids.

According to the invention, inactivating micro-organisms means any bactericidal or bacteriostatic effects.

By selectively inactivating of the corynebacteria only those corynebacteria capable of metabolising fatty acids is meant inactivating corynebacteria A to a significantly higher degree than corynebacteria B. Preferably it means inactivating corynebacteria A to a significantly higher degree than the majority, preferably at least 75%, more preferably at least 90% of bacteria other than corynebacteria A constituting the skin microflora.

The active employed in the present invention can suitably be an antimicrobial agent which is more active against corynebacteria A than against corynebacteria B. Preferably the antimicrobial is more active against corynebacteria A than against the majority of other bacteria constituting the skin microflora including corynebacteria B.

The following is an inexhaustive list of active agents according to the invention:

1. esters;
2. antimicrobial agents targeted to corynebacteria A by antibodies, antibody fragments and hydrophobic proteins.

1. Esters:

Preferably the ester comprises at least one moiety capable of inactivating of the corynebacteria only those corynebacteria capable of catabolising fatty acids. For example, the ester may be an ester of an acid with the above described inactivating capability and a non-inactivating alcohol. The ester may equally be an ester of an acid without an inactivating capability and an inactivating alcohol. The ester may also comprise an inactivating alcohol and inactivating acid. Further examples of suitable esters may also include esters with a mixture of acids and alcohols all or only some of which having an inactivating capability. Optional substituents include methoxy and hydroxy groups.

Examples of suitable acids include:

fatty acids, which may be branched or unbranched, saturated or unsaturated, substituted or unsubstituted, monocarboxylic acids, e.g. C2–C24, particularly C6–C16 fatty acids, such as decanoic acid and dodecanoic acid, or polycarboxylic acids, e.g. dicarboxylic acids, containing from 2 to 40, preferably from 10 to 22 carbon atoms, e.g. monounsaturated dioic acids, such as C18:1 dioic acid; saturated dioic acids, such as azelaic acid;

aryl acids such as phenyl acids, e.g. ferulic acid and cinnamic acid; benzoic acid.

Examples of suitable alcohols include:

monohydric alcohols, e.g. fatty alcohols which may be branched or unbranched, saturated or unsaturated, substituted or unsubstituted, containing from 2 to 40, preferably from 10 to 20 and more preferably from 14 to 18 carbon atoms, e.g. palmityl alcohol; and polyhydric alcohols, which include:
α-ω dihydric alcohols containing from 2 to 20 carbon atoms, such as butanediol and dodecanediol;
glycerol,
mono or poly propylene glycol, mono or poly ethylene glycol;
sugars, such as glucose; and substituted sugars, such as alkyl glucosides, e.g. ethyl glucoside.

The ester may be a monoester of a polyester.

Examples of esters according to the invention are: C18:1 dioic acid butanediol polyester, C18:1 dioic acid dodecanediol polyester, bisglycerol C18:1 dioic acid ester, bisglucose C18:1 dioic acid ester, C12 ethyl glucoside ester, hexadecyl ferulate, and C8–14 fatty acid triglycerides, e.g. tricaprylin, tricaprin, trilaurin and mixtures thereof.

Where the active is C18:1 dioic acid butanediol polyester it has a molecular weight ranging from 800 to 50000, preferably from 1500 to 20000 and more preferably from 2500 to 10000.

2. Antimicrobial agents targeted with antibodies or hydrophobic proteins:

By antibody is meant any complete antibody or a fragment thereof, which has a selective affinity to corynebacteria A.

Examples of hydrophobic proteins include oleosins.

Examples of antimicrobial agents include all known cosmetically acceptable antimicrobial agents.

Antibodies or antibody fragments can be employed to deliver active agents to target sites, with provision for binding to those target sites. In the invention herein, the target sites are cell-surface antigens of Corynebacterium A species. The active agent may be connected to the antibody or antibody fragment by a variety of means, e.g. chemical conjugation.

The active agent according to the present invention may preferably be employed in a composition which may be applied to human skin for the reduction or elimination of body malodour. Examples of products comprising an active agent according to the invention include antiperspirants, deodorants, shampoos, conditioners, skin cleansers, detergents, hair conditioners, sunscreens, sun tan lotions, skin conditioners, etc. It is to be understood that this list is not exhaustive with regard to suitable products comprising active agents according to the invention.

Typical deodorant compositions comprising an active agent according to the invention may also comprise other materials commonly found in underarm compositions such as deodorant or antiperspirant compositions, for example, cosmetically acceptable vehicles; deodorant actives; perfumes; antiperspirant actives; skin benefit agents; colours; water; humectants and other cosmetic adjuncts conventionally employed in such compositions. The use of such substances depends on the form of the composition which may be an aerosol, stick, roll-on, gel, lotion, cream, ointment, powder, suspension or soap.

The active agent may be used in an amount effective to inactivate, of corynebacteria, only those corynebacteria capable of catabolising fatty acids. Usually the active agent may be present in an amount ranging from 0.001 to 10% by weight of the composition, and preferably from 0.01 to 2%.

EXAMPLE 1

The demonstration of fatty acid catabolism in a particular bacterial strain was determined in vitro using the method given below:

The in vitro model system, reproducing fatty acid catabolism by axillary bacteria, consisted of 250 ml baffled shake flasks, to which were added 30 ml semi-synthetic medium (see below) supplemented with fatty acid substrate (2.0 mg/ml pentadecanoic acid) and non-fatty acid substrate (0.5–1.0 mg/ml glucose). This system was employed to distinguish between fatty acid catabolising species of corynebacteria and non-fatty acid catabolising species of corynebacteria. Flasks were inoculated with fresh bacterial biomass, pre-grown for 24 h in TSBT (see below), to give starting optical densities ($A_{690}$) of 1.0–2.0. Following inoculation, flasks were incubated aerobically at 35° C., with agitation (130 rpm), and analysed after 24 h. Culture viability/purity was determined by TVC analysis on TSAT plates (see below) following serial dilution in quarter-strength Ringers solution. Fatty acids were determined by capillary gas chromatography (GC) (see below). Residual glucose concentrations were measured with blood glucose test strips (BM-Test 1-44; Boehringer Mannheim) used in conjunction with a Reflofux™s glucose meter (Boehringer Mannheim).

Fatty acid levels in the flasks were determined by capillary GC analysis. Initially, 5.0 ml aliquots from each flask were rapidly transferred into universal tubes; an internal standard (1.0 mg/ml lauric acid) was added to each universal and the culture medium was acidified (pH ~2) by the addition of hydrochloric acid. Liquid—liquid extraction was then carried out using 2 vol (10 ml) ethyl acetate; organic and aqueous phases were resolved by centrifugation (2000 rpm, 3 min). 2.0 ml of each organic (upper) phase was then transferred to a sampling tube prior to analysis on a Perkin Elmer 8000 (Series 2) GC fitted with a 15 m×0.32 mm (internal diameter) FFAP (nitroterephalic acid modified PEG/siloxane compolymer) fused silica capillary column (film thickness 0.25 $\mu$m) (Quadrex). This column was attached to the split-splitless injector and flame ionisation detector (FID) of the GC; injector and detector temperatures were each 300° C. Carrier gas for the column was helium (6.0 psi), while hydrogen (17 psi) and air (23 psi) supplied the FID. The temperature programme for fatty acid analysis was 80° C. (2 min); 80–250° C. (20° C./min); 250° C. (5 min). Sample size for injection was 0.5–1.0 $\mu$l. Fatty acid levels in the flasks were quantified by comparison of peak areas with known levels of both internal (lauric acid) and externally-run (pentadecanoic acid) standards.

Composition of Tween-supplemented Tryptone soya broth (TSBT) used for growth/maintenance of axillary bacteria (g/l): Tryptone soya broth (30.0)(Merck), Yeast extract (10.0) (Beta Lab), Tween 80 (1.0) (Tween is a trade mark of ICT Speciality Chemicals). Composition of semi-synthetic medium used in laboratory systems simulating fatty acid catabolism by axillary bacteria (g/l): $KH_2PO_4$ (1.6), $(NH_4)_2HPO_4$ (5.0), $Na_2SO_4$ (0.38), Yeast Nitrogen Base (Difco) (3.35), Yeast Extract (0.5), Tween 80 (0.2), Triton X-100 (0.2), $MgCl_2.6H_2O$ (0.5), Glucose (0.5–1.0), Pentadecanoic acid (2.0).

EXAMPLE 2

The ability of esters to selectively inactivate corynebacteria A was determined in vitro using the conditions given below:

The experiments were carried out in 7 ml glass screw-capped vials containing a 4 ml emulsion of active in potassium phosphate buffer, inoculated with 1 ml of a washed suspension of an axillary isolate of corynebacteria A (NCIMB 40928) or corynebacteria B (NCIMB 40929). The inoculum of corynebacteria A or B was prepared by culturing bacteria in growth medium for 36 h then adding high oleate sunflower oil (1 g/l final concentration) and culturing the organisms for a further 48 h. After this time, the organisms were harvested by centrifugation (at 3000 rpm for 15 min), washed twice and resuspended in potassium phosphate buffer (10 mM, pH 6.0) supplemented with 0.2 g/l Tween 80, to give a final OD ($A_{590}$) in the experimental vial of 7–8. Preparation of the active emulsion is described below. The vials were incubated at 35° C. with agitation (100 rpm), and sampled at specific time intervals.

Viability of the Corynebacterium cultures was assessed by viable counting on TSAT (see below) plates following serial dilution in quarter strength Ringers solution, and incubation at 35° C. for 2–3 days. Growth medium used for the preparation of the Corynebacterium inoculum was composed of 200 ml of tryptone soya broth (20 g/l), yeast extract (10 g/l), and Tween 80 (2.5 g/l). The active emulsion was prepared using potassium phosphate buffer (10 mM, pH 6.0), supplemented with Tween 80 (0.2 g/g), Triton X-100 (trademark of Union Carbide) (5 g/l), and the selected ester. An emulsion was prepared by homogenization. TSAT medium used for the viability assessment of Corynebacterium species was composed of tryptone soya broth (30 g/l), yeast extract (10 g/l), Tween 80 (1.0 g/l) and agar (20 g/l).

The selective inactivation of corynebacteria A by a fatty acid polyester, a polyester of 9-octadecenedioic acid and butanediol (abbreviated to C18:1 polyester), compared to the non-antimicrobial effect on corynebacteria B is summarised in Table 1 and presented in FIG. 1.

TABLE 1

| Bacterium | C18:1 polyester (g/l) | Viability ($log_{10}$ CFU/ml) After Time (h) | | | |
| --- | --- | --- | --- | --- | --- |
| | | 0 | 2 | 4 | 6 |
| Corynebacterium A | 0.0 | 9.26 | 9.28 | 9.23 | 9.20 |
| (NCIMB 40928) | 1.0 | 9.26 | 9.20 | 7.79 | 3.77 |
| Corynebacterium B | 0.0 | 9.28 | 9.26 | 9.32 | 8.18 |
| (NCIMB 40929) | 1.0 | 9.28 | 9.32 | 9.23 | 8.20 |

The controls clearly show that the reduction in viability of the corynebacteria B is not caused by the presence of the active agent. Similar results have been obtained with medium chain (C8-10) fatty acid triglycerides as the inactivating esters.

EXAMPLE 3

The following is a typical formulation which comprises an agent capable of inactivating body malodour causing microorganisms comprising corynebacteria, characterised in that the agent is capable of inactivating, of the corynebacteria, only those corynebacteria capable of catabolising fatty acids.

It is made by methods common in the art.

| Ingredient | Content % by weight |
| --- | --- |
| Ethanol | 56.5 |
| $C_{8-10}$ fatty acid triglycerides | 1.00 |
| Isopropyl myristate | 1.0 |
| Fragrance | 1.5 |
| Propellant | 40.0 |

What is claimed is:

1. A method for reducing or preventing body malodour which comprises topically applying to human skin an active agent capable of inactivating through bactericidal or bacteriostatic effects, body malodour-causing microorganisms comprising only those corynebacteria capable of catabolising fatty acids.

2. A method according to claim 1 wherein the active agent is an ester.

3. A method according to claim 2 wherein the ester comprises at least one inactivating moiety.

4. A method according to claim 3 wherein the active agent is a mono or polyester of a polyhydric alcohol and a dicarboxylic acid.

5. Cosmetic method according to claim 1 wherein the active agent is selected from the group consisting of C18:1 dioic acid butanediol polyester, tricaprylin, tricaprin and trilaurin or a mixture thereof.

* * * * *